US007098672B2

United States Patent
Belyakov et al.

(10) Patent No.: US 7,098,672 B2
(45) Date of Patent: Aug. 29, 2006

(54) FLASH VAPOR SAMPLING FOR A TRACE CHEMICAL DETECTOR

(75) Inventors: Vladimir V. Belyakov, Lynn, MA (US); Stephen N. Bunker, Wakefield, MA (US)

(73) Assignee: Implant Sciences Corporation, Wakefield, MA (US)

( * ) Notice: Subject to any disclaimer, the term of this patent is extended or adjusted under 35 U.S.C. 154(b) by 9 days.

(21) Appl. No.: 10/890,820

(22) Filed: Jul. 14, 2004

(65) Prior Publication Data
US 2005/0007119 A1    Jan. 13, 2005

Related U.S. Application Data

(63) Continuation-in-part of application No. 10/349,491, filed on Jan. 22, 2003, now Pat. No. 6,828,795, and a continuation-in-part of application No. 10/853,563, filed on May 25, 2004.

(60) Provisional application No. 60/473,649, filed on May 29, 2003.

(51) Int. Cl.
*G01R 27/04* (2006.01)
*G01N 25/00* (2006.01)

(52) U.S. Cl. ...................................... 324/646; 324/451
(58) Field of Classification Search ................ 324/646, 324/451
See application file for complete search history.

(56) References Cited

U.S. PATENT DOCUMENTS

| 5,206,594 A | * | 4/1993 | Zipf ........................... 324/464 |
| 5,311,010 A | * | 5/1994 | Kruger ................. 250/214 VT |
| 6,448,562 B1 | * | 9/2002 | Seidler et al. .............. 250/372 |
| 2002/0158211 A1 | * | 10/2002 | Gillispie .................. 250/458.1 |

OTHER PUBLICATIONS

U.S. Appl. No. 10/754,088, filed Jan. 7, 2004, Virtual Wall Gas Sampling for an Ion Mobility Spectrometer, Krasnobaev et al.
U.S. Appl. No. 10/818,434, filed Apr. 5, 2004, Modified Vortex for an Ion Mobility Spectrometer, Krasnobaev et al.

* cited by examiner

*Primary Examiner*—Vincent Q. Nguyen
(74) *Attorney, Agent, or Firm*—Muirhead and Saturnelli, LLC

(57) ABSTRACT

The presence of trace molecules in air is often determined using high sensitivity gas sensing instruments, such as an ion mobility spectrometer. Such devices are commonly utilized in the fields of explosives detection, identification of narcotics, and in applications characterized by the presence of very low airborne concentrations of organic molecules of special interest. The sensitivity of such instruments is dependent on the concentration of target gas in the sample. The sampling efficiency can be greatly improved when the target object is warmed, even by only a few degrees. A directed emission of photons in the range between infrared and ultraviolet light can be used to significantly enhance vapor emission.

16 Claims, 5 Drawing Sheets

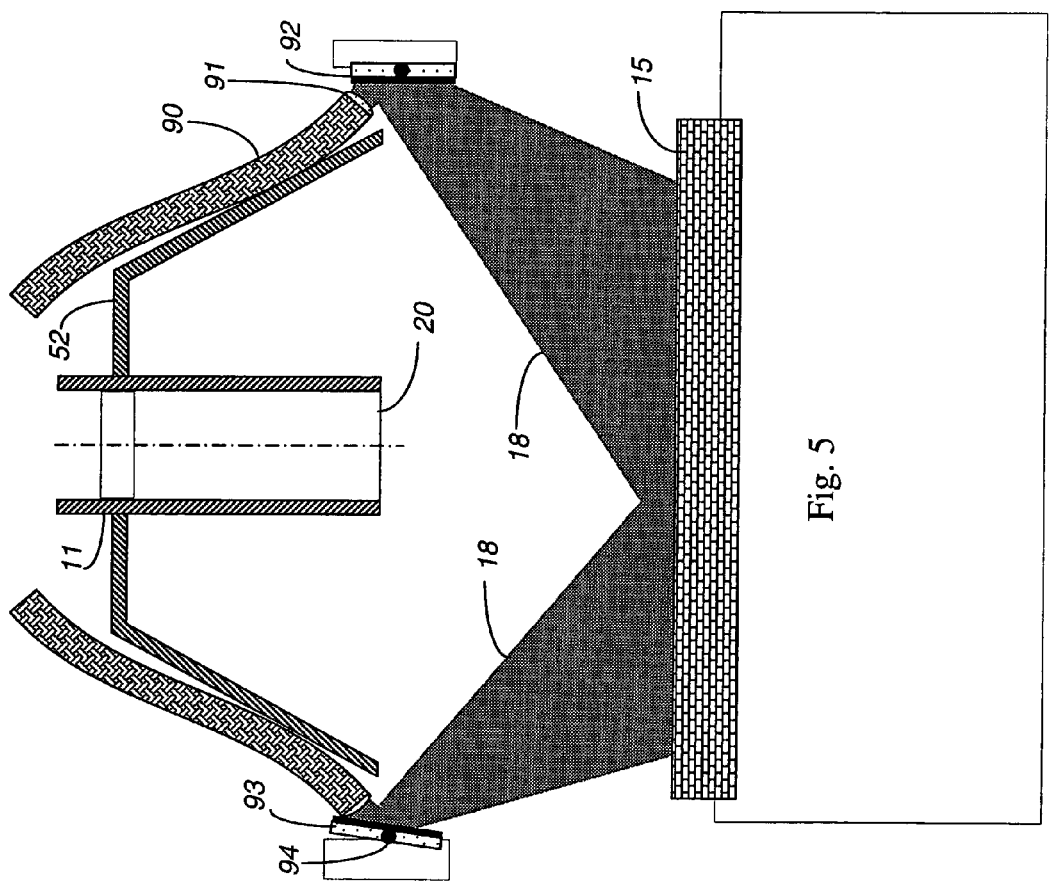

FLASH VAPOR SAMPLING FOR A TRACE CHEMICAL DETECTOR

CROSS-REFERENCE TO RELATED APPLICATIONS

This application is a continuation-in-part of U.S. patent application Ser.No. 10/349,491 filed on Jan. 22, 2003 now U.S. Pat. No. 6,828,795, which claims priority from U.S. patent application Ser. No. 10/295,039 filed on Nov. 14, 2002, which claims priority from U.S. Provisional Application No. 60/357,394, filed Feb. 15, 2002, U.S. Provisional Application No. 60/357,618, filed Feb. 15, 2002, and U.S. Provisional Application No. 60/363,485, filed Mar. 12, 2002, all of which are incorporated herein by reference. This application is also a continuation-in-part of U.S. patent application Ser. No. 10/853,563, filed May 25, 2004, which claims priority from U.S. Provisional Patent Application Ser. No. 60/473,649, filed May 28, 2003, both of which are incorporated herein by reference.

FIELD OF THE INVENTION

This invention relates to a trace chemical vapor detection instrument that detects chemicals present as vapors in air or other gases, or liberated as vapors from condensed phases such as particles or solutions. It particularly relates to increasing the sampling concentration of such vapors for injection into a trace chemical vapor detector using pulsed photonic energy.

BACKGROUND OF THE INVENTION

Many well-known instruments are used to measure the presence of trace chemical vapors in the atmosphere. Examples of such instruments include, but are not limited to, gas chromatographs (GC), ion mobility spectrometers (IMS), mass spectrometers (MS), microsensors based on gas adsorption onto a mass-sensitive surface, electron capture detectors, sensors that use optical stimulation to provide a characteristic emission wavelength for detection, and microsensors based on changes in semiconductor properties when gas adsorbs onto their surfaces. Such instruments may operate in real time by causing one or more flowing streams of gas to enter the instrument through one or more orifices, and the gas may exit through one or more different orifices. At least one of the flowing gas streams entering the instrument includes gas that has been sampled (the "sample gas") from the surrounding atmosphere or other source of vapor to be analyzed. Alternately, the sample gas may first be allowed to interact with a temporary adsorbing surface in order to concentrate the vapor sample. An example of such an adsorbing surface used with a GC is called a solid phase microextraction fiber (SPME), and special chemical coatings are used to enhance the adsorption of sample vapor. Many other types of vapor concentrators are well known in the art. At some later time a second step is to heat the adsorbing surface by various means in order to desorb the concentrated sample gas into the instrument for measuring trace chemical vapors. The adsorbent surface may also be optionally moved to a separate location prior to desorption. This two step process is operationally equivalent to the real time sample gas acquisition process as a method of acquiring a vapor sample for the vapor detection instrument.

In some cases, the process of taking a sample begins with an operator rubbing an absorbent substance, such as chemical filter paper, onto the surface to be tested. Particles of the chemical of interest may then be transferred and concentrated on the absorber. This intermediate absorber is then brought to the vicinity of the sampling orifice of the IMS. The method of concentrating using an absorbent substance tends to be relatively slow to implement and is subject to variations in the skill of the operator. Additionally, while the absorber is relatively low in cost, the process of taking a great many samples becomes expensive in that the absorber generally should only be used once to ensure consistent results.

The quantity of particles of the target substance on the target surface is usually very small, often corresponding to only nanograms or even picograms of particles per square centimeter. The detection instrument may need to be very sensitive to identify a positive signal from evaporated target molecules when the initial concentration and surface area of target particles is small.

A sampling method that is employed is to provide a gas pump, which draws the sample gas into the detection instrument through a tube. For example, the pump may be disposed to provide a partial vacuum at the exit of an ion source that is a component of the instrument. The partial vacuum is transmitted through the confines of the ion source and appears at the entrance orifice of the ion source. A further tubulation may be provided as an extension to a more conveniently disposed sampling orifice external to the instrument. The operator places a sample in the near vicinity of this external sampling orifice, and the ambient vapor is drawn into the gas flow moving towards the ion source.

The instrument may provide a signal that is approximately proportional to the concentration of target molecule vapor. This concentration is further dependent on the equilibrium vapor pressure of the target molecule, the temperature of the target molecule where it is emitting the vapor, the total flow rate of non-target gas that dilutes the target vapor, and possible adsorption losses on surfaces of the gas sampling system. Existing systems that utilize an adsorbent or particle-collecting surface concentrator sometimes employ an oven to greatly warm the adsorbent material, often up to 200 degrees Centigrade, and thereby increase the target vapor concentration.

In some circumstances, it is desirable for instruments to be able to sample vapors at a distance from the external sampling orifice. Examples may include, but not be limited to, sampling of vapor from complex surfaces that contain many holes, crevices, or deep depressions, textured materials such as cloth, people and animals that prefer not to be rubbed by absorbent material, large three dimensional objects, surfaces that must be sampled in a short time, and surfaces in which surface rubbing by human operators is inconvenient or expensive. In addition, it has been observed that the sampling orifice may become contaminated with vapor-emitting particles if the sample inadvertently contacts the orifice. Such contamination is particularly difficult to remove in a short period of time, thus preventing continuous operation of the instrument. Such contamination could be avoided if vapors are sampled at a distance from the sampling orifice.

The distance where vapors may be sampled beyond the sampling orifice may be increased by increasing the sample gas flow rate, i.e., increasing the pumping speed. However, besides the interference with the performance of the instrument for measuring trace vapors caused by high velocity flow, this method dilutes the concentration of the desired sample vapor by mixing in a much larger volume of ambient gas. Therefore, the sensitivity of the instrument may decline if the sample gas flow rate is increased excessively.

Warming surfaces at a distance using an oven is generally not very efficient. While warmed gas can be blown onto a distant surface, for example with a "heat gun", when the target surface is a living person or animal, this may not be an acceptable option. Additionally, many surfaces cannot tolerate excessive heating and may be damaged.

SUMMARY OF THE INVENTION

According to the present invention, a system for inducing increased emission of target vapor for a vapor detection instrument includes a source of pulsed photon emission at a range of wavelengths substantially in the infrared to ultraviolet portion of the spectrum, a wave concentrator that concentrates the photon emission into a beam, and a wave guide that directs the photon emission towards a target surface. The source of pulsed photon emission may be at least one of: a light emitting diode and an electrical discharge in a gas. The source of photon emission may be at least one of: pulsed and keyed to form a pulse less than 100 milliseconds in duration. The wave concentrator may include at least one of a mirror, lens, and fiber optic waveguide. The wave guide may include at least one of a mirror, lens, and fiber optic waveguide. The wave guide may be adjusted, e.g., moved or tilted, to increase the area capable of being illuminated by the photon emission. The external photon emission may be distributed substantially within a portion of the band of wavelengths naturally emitted by the source of photon emission by means of at least one of a filter, coating, and covering. The source of photon emission may have enhanced emission substantially in the infrared by means of conversion of shorter wavelength photons to infrared photons. The source of photon emission may be separated from the target surface by at least one of a window and a semi-transparent grid. The process of inducing emission of target vapor is also referred to as desorption of target vapor when the target chemical is adsorbed onto the surface of some inert substrate.

According further to the present invention, a system for inducing increased emission of target vapor for a vapor detection instrument includes a gas sampling inlet that samples vapors from a target and provides the vapors to the instrument or a vapor concentrator for said instrument and a source of photons, mounted proximal to the gas sampling inlet, the source of photons providing photonic emissions to the target in connection with the inlet sampling vapors. The photonic emissions may be at multiple wavelengths substantially in the infrared to ultraviolet portion of the spectrum. The source of photon emission may be made to be substantially in the infrared or other portion of the spectrum using at least one of a filter, coating, and covering. The source of photon emission may have enhanced emission substantially in the infrared or other portion of the spectrum by means of conversion of shorter wavelength photons to longer wavelength photons. The photonic emissions may be provided by at least one of a light emitting diode and an electrical discharge in a gas. The source of photon emission may be at least one of: pulsed and keyed to form a pulse less than 100 milliseconds in duration. The source of photon emission may be separated from the target surface by at least one of a window and a semi-transparent grid.

The invention applies to a vapor detection instrument that uses an external sampling orifice to draw in vapors to be analyzed. A method for inducing increased emission of target vapor from a distant target surface is described using at least one of several techniques. The goal is to heat the target chemical surface in a manner such that the action of heating is unobtrusive, perhaps invisible, the sampled portion of the surface is warmed at least 5 degree C., and only the surface is warmed, not the bulk of the target material. These conditions may be accomplished using one or more pulsed sources of photons. A light source that is substantially in the infrared portion of the spectrum has the advantage that it is largely invisible to the eye, except for a slight reddish appearance. However, brighter light sources, that warm the surface more quickly, can be produced using visible and ultraviolet photons in addition to infrared photons. Infrared wavelengths are generally considered to be longer than 750 nanometers and shorter than 100 micrometers. Visible wavelengths are generally considered to be in the range of 750 nanometers to 370 nanometers. Ultraviolet wavelengths are generally considered to be in the range of 370 nanometers to 10 nanometers. Most sources of visible light produce a small percentage of ultraviolet light less than 370 nanometers and some small percentage of infrared light. Most light sources, except lasers, produce a range of wavelengths, and a source is considered to be a visible light source if the peak of its distribution is in the visible range of wavelengths.

Apparatus may be employed for guiding and concentrating the photon beam from the light source towards a place on the target surface where gas sampling is more efficiently being performed in order to minimize the power consumption, heat primarily the target surface of interest, and maximize the lifetime of the light source. This apparatus may be in the form of one or more lenses, one or more mirrors, fiber optic cable, or some combination of these. An example may include a parabolic mirror combined with a nearly point source of light. With the point source situated near to the focal point of the mirror, a substantially parallel photon beam results, which can then be directed at the desired location on the target surface.

There are many well-known sources of light that may be utilized. An example of a pulsed light source is a xenon flash lamp, in which the pulse duration in one embodiment is approximately 0.1 milliseconds. Light emitting diodes are available as focused arrays within a package with a built-in lens.

The source of light may be pulsed or keyed to form a pulse less than 100 milliseconds in duration. Pulsed light has the advantage of conserving energy and avoiding overheating of the target surface. Pulsed light has the further advantage of warming the target surface in a very short time period, thus causing the emitted target vapor to mix with a smaller portion of ambient air before being drawn into the gas sampling orifice. This enhances the target vapor concentration by reducing dilution. A further desirable feature is that the pulsed light source is off when not in use, thus saving energy. A continuous output light source requires time to come to stable operating conditions and thus is slow to pulse. An alternate embodiment would be to combine a shutter with a continuous output light source in order to simulate a pulsed source, but a naturally pulsed light source is usually brighter than a continuous light source with a shutter for an equal average power consumption. Equivalently, a continuous source of light may be pulsed on with a pulse duration less than 100 milliseconds, and this is sometimes referred to as "keyed". An example of such a source of light is a light emitting diode or a plurality of such diodes, which emit photons only when a voltage pulse is applied. A laser is less desirable for this application in that the laser beam is typically very small in cross section and must be scanned across a surface in a raster pattern to illuminate a large area. Lasers are also more expensive than xenon lamps or light emitting diodes.

According further to the present invention, the pulse of photons that induce desorption of the target vapor may be less than 100 milliseconds and may comprise a range of wavelengths between the infrared and ultraviolet. The lamp that provides an electrical discharge in a gas that produces the pulse of photons may contain an inert gas, such as xenon, krypton, neon, or a mixture of inert gases. The energy for the pulse of photons may be provided by the discharge of a high voltage capacitor through an electronic circuit.

In one embodiment, a high brightness pulsed lamp, such as a xenon-filled lamp, is used to illuminate the adsorbing surface for a time period less than 100 milliseconds, for example, less than 1 millisecond. The energy transmitted by the pulse of photons from the lamp to the target surface may be much smaller than that required to heat the entire substrate of the target surface to a given temperature. Still, the surface layer of the target surface, which only includes a few hundred monolayers of atoms, may not conduct this sudden influx of energy away instantaneously, and thus the target surface may momentarily become relatively warm. The effect might last only for a few milliseconds before thermal conduction dissipates the energy into the substrate of the target material, and the surface layers cool off.

The interaction of the light radiation with the particles of target material depends on the wavelength of radiation employed. At some wavelengths, the target particles may substantially reflect or transmit the incident radiation, thus not absorbing energy and becoming warmed. Heating is then accomplished indirectly by using the incident radiation to warm the surface on which the target particles or adsorbed vapor are attached with heat being transferred to the target particles or adsorbed vapor by conduction, convection, or conversion of the incident wavelength to one that is substantially longer where the target molecules are more absorptive.

BRIEF DESCRIPTION OF THE DRAWING

The invention is described with reference to the several figures of the drawing, in which.

FIG. 5 is a schematic showing an exemplary embodiment for scanning a photon beam or beams using one or more moving hot mirrors.

DETAILED DESCRIPTION OF CERTAIN PREFERRED EMBODIMENTS

Figure 1:
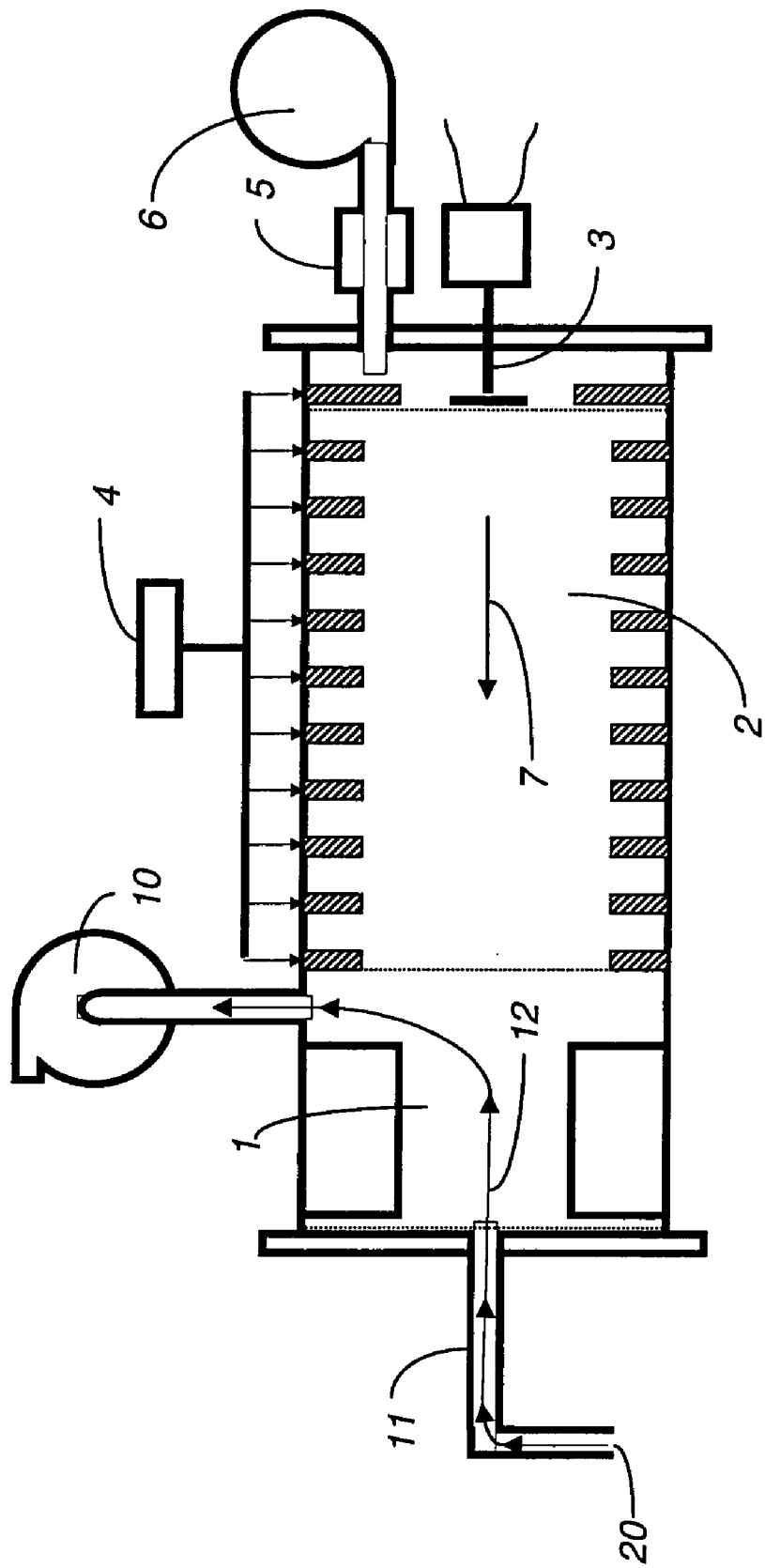
FIG. 1 is a schematic of an IMS trace vapor detection instrument that may be used in connection with the system disclosed herein.

An IMS is illustrated in FIG. 1. While various embodiments may differ in details, FIG. 1 shows basic features of an IMS that may be used in connection with the system described herein. The IMS includes an ion source 1, a drift tube 2, a current collector 3, a source of operating voltage 4 and a source of purified drift gas 5, possibly with its own gas pump 6. An IMS may already include a gas pump for gas sampling 10 and a tubular connection 11 between the ion source 1 and an external gas sampling inlet 20 that includes an orifice. Gas flow for the drift gas 7 moves through the drift tube 2. Sampling gas flow 12 moves from the external gas sampling inlet 20 through the tubular connection 11 and ion source 1 to the gas sampling pump 10.

Figure 2:
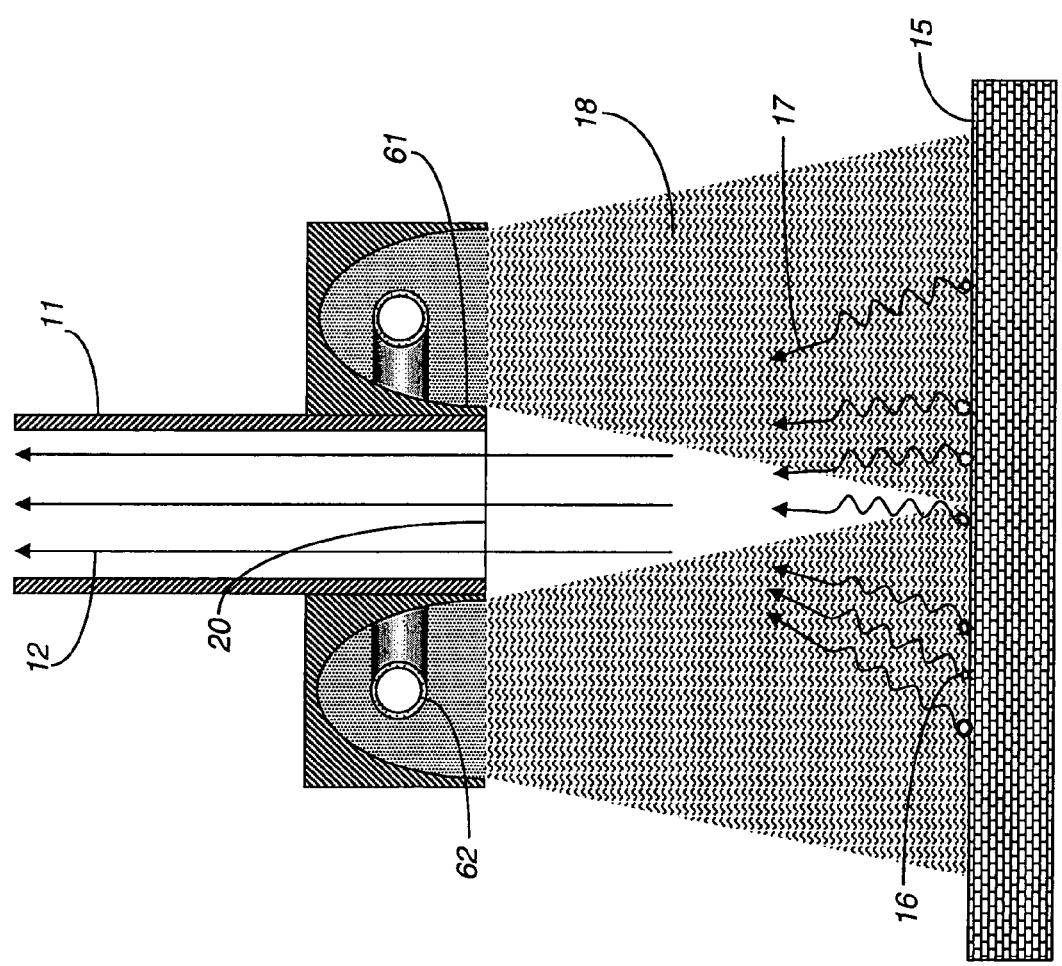
FIG. 2 is a schematic diagram showing an exemplary embodiment for a system using an electrical discharge in a gas within a pulsed light lamp that is located near the focus of a parabolic reflector to induce increased emission of target vapor for a vapor detection instrument.

FIG. 2 shows an exemplary embodiment for a system using an electrical discharge in a gas within a pulsed light lamp 62 provided proximal to the gas sampling inlet 20 that heats the target surface 15 in conjunction with the gas sampling system of the vapor detection instrument. A parabolic reflector 61 is used as a wave concentrator to concentrate the photons from the pulsed light lamp 62. The reflector 61 may optionally be polished and optionally coated with a reflective material. The figure shows a single circular lamp 62, but other embodiments may use a plurality of linear or coiled shapes. The reflector 61 may be disposed to produce a beam that is substantially parallel to the axis of tubular connection 11 or optionally tilted to alter the area on target surface 15 that is primarily illuminated.

Target surface 15 may be covered with target particles 16 or equivalently with an adsorbed coating of target chemical. The photon emission 18 reaching the target surface 15 heats the target surface or equivalently heats the target particles 16 in order to increase vapor emission 17. Vapor emission 17 is entrained within the flow of ambient gas becoming the sample gas flow 12 into the vapor detection instrument.

Figure 3:
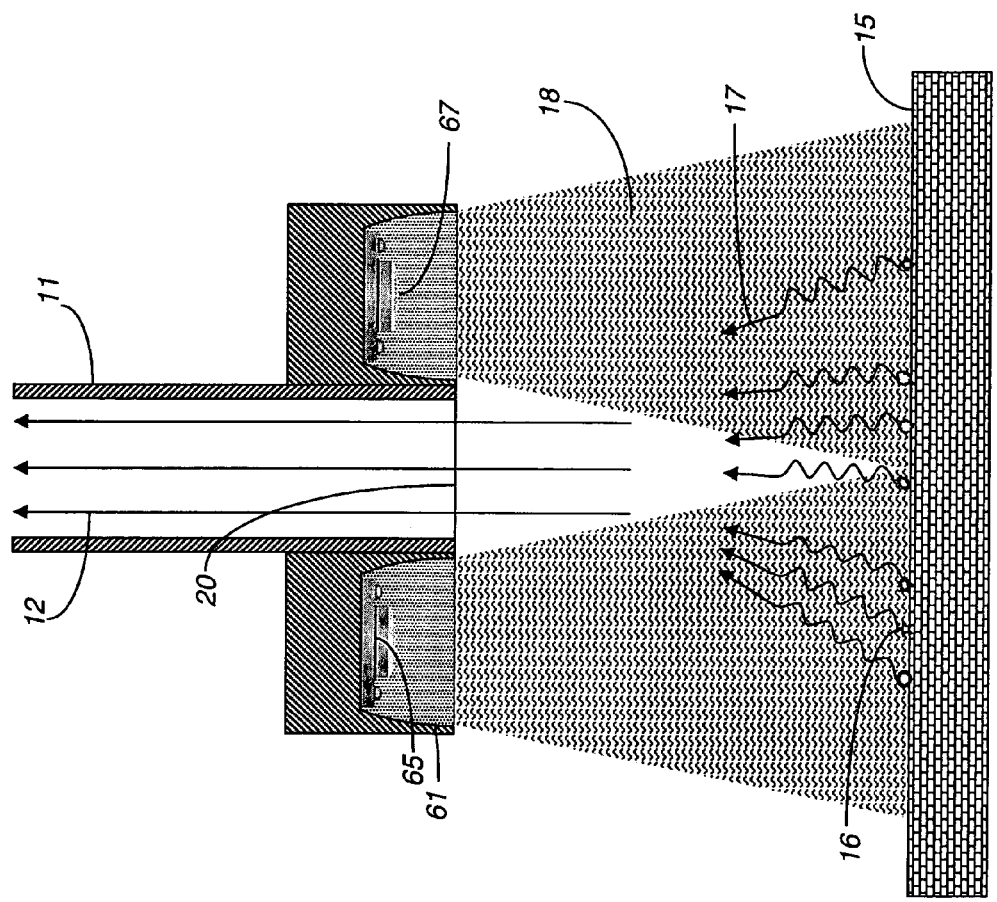
FIG. 3 is a schematic diagram showing an exemplary embodiment for a system using a plurality of keyed light emitting diode arrays with optical communication provided by a lens integrated with each array to induce increased emission of target vapor for a vapor detection instrument.

FIG. 3 shows an exemplary embodiment in the form of an array of light emitting diodes 65. These may optionally be an array of individually packaged diodes or a plurality of packages that internally contain many diodes, as shown in the figure. The diodes 65 are provided proximal to the gas sampling inlet 20. The photon emission may be directed to target surface 15 by employing at least one of reflector 61 and lens 67 as a wave guide. The photon beams 18 impinge onto the target surface 15, heating target particles 16 and causing the enhanced emission of target molecule vapors 17. The target molecule vapors 17 are entrained in the gas flow 12 entering the gas sampling inlet 20. Different numbers of the same or different types of heating modules may be used. Light emitting diodes often are caused to emit pulsed light using pulsed applied voltage, a process referred to as a keyed pulse.

Figure 4:
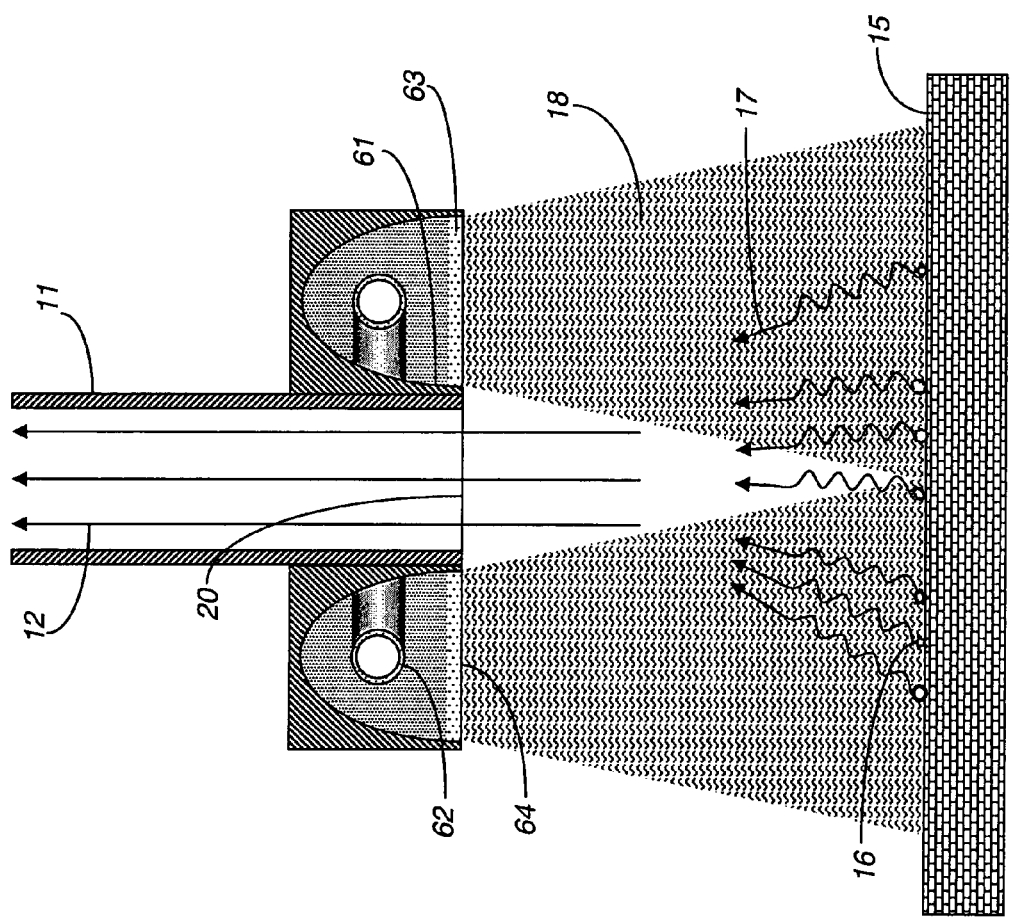
FIG. 4 is a schematic diagram showing an exemplary embodiment for transmission of the photon beam through an optical window with a coating used as a filter to limit the band of wavelengths transmitted to the target surface.

FIG. 4 shows an exemplary embodiment utilizing a window 63 with a coating 64 covering the source of photons 62. Light sources that produce a broad spectrum of wavelengths may optionally be coated, filtered, or covered with infrared-enhancing materials in order to increase the infrared fraction of the output spectrum. Such materials may act as transmission filters in which the infrared component is selectively passed, or they may alternatively convert a portion of the incident shorter wavelength light photons to infrared photons, possibly by heating a secondary surface to a high temperature. Similarly, glass bulbs that have substantial output in visible or ultraviolet light may have surface coatings, both internal or external, internal gases, or filters to increase the infrared fraction of the output spectrum. The filter, coating, or covering may optionally be in the form of a mirror that selectively reflects infrared, commonly called a "hot mirror". Alternatively, the filter, coating, or covering may be a "cold mirror" that reflects visible but transmits infrared, particularly as a protective window. Such protective windows are useful for isolating hot or delicate sources of light radiation. In addition to a cold mirror, a transparent window or open mesh grid may also be used as a protective window.

FIG. 5 shows other possible embodiments for transmitting the photon beam or beams to the target surface 15. Fiber optic light guides 90 are disposed proximal to the tubular connection 11 to the vapor detection instrument and to the gas sampling inlet 20. In the embodiment shown, a lens 91 is employed to minimize the divergence of the photon beam 18 being emitted by the fiber optic cable 90. The photon beams 18 are aimed at positions on the target surface 15 to enhance the emission of target molecule vapor. The positions may optionally be selected to overlap and reinforce one another or to illuminate separate locations.

Fiber optics or similar light guides may be used to separate the location of light generation and the illumination of the target surface to permit physically larger lamps than would be possible nearer to the sampling inlet 20. Moving mirrors 93 may be used to scan the photon beam 18 in order to define a larger irradiated surface area. A variable focus lens or the position of the optical source relative to the mirror may be utilized to change the optical beam cross section or to selectively focus the optical beam at a particular distance. Alternatively, hot mirrors 92 reflect the photon beam 18 emitted from fiber optic cables 90. A lens 91 is employed to focus the photon beam 18, although in an alternate embodiment the hot mirror 92 could have a concave surface to accomplish similar focusing control. The hot mirrors 92 may also be optionally tilted about axis 94 in order to scan the photon beam 18 across the target surface 15.

Other methods of optical emission, transmission, filtering, and focusing are possible, and the specifically described embodiments should not be understood as restricting the scope of the invention. In addition, one skilled in the art will recognize that the flash vapor sampling apparatus described herein may easily be adapted for use with other vapor detection instruments appropriate for measuring trace chemical vapors, including but not limited to gas chromatographs, mass spectrometers, microsensors based on gas absorption onto a mass-sensitive surface, electron capture detectors, sensors that use optical stimulation to provide a characteristic emission wavelength for detection, and microsensors based on changes in semiconductor properties when gas adsorbs onto their surfaces.

The vapor detection instruments described herein may incorporate other novel features, such as the cyclone sampling described in copending and commonly assigned U.S. application Ser. No. 10/295,010, filed Nov. 14, 2002, or the electrostatic particle sampling system described in copending and commonly assigned U.S. application Ser. No. 10/349,491, filed Jan. 22, 2003, the contents of both of which are incorporated by reference herein.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A system for inducing increased emission of target vapor for a vapor detection instrument comprising:
    a pulsed source of photon emission that generates a pulsed photon emission having multiple wavelengths contained substantially within the infrared to ultraviolet;
    a wave concentrator that concentrates said pulsed photon emission into a beam; and
    a wave guide that directs said beam towards a target surface to heat the target surface with the pulsed photon emission having multiple wavelengths to increase vapor emissions from the target surface.

2. The target vapor emission system of claim 1, wherein said source of photon emission is at least one of: light emitting diode and an electrical discharge in a gas.

3. The target vapor emission system of claim 1, wherein said source of photon emission is at least one of: pulsed and keyed in a pulse.

4. The target vapor emission system of claim 3, wherein said pulse of photon emission is less than 100 milliseconds in duration.

5. The target vapor emission system of claim 1 wherein said wave concentrator includes at least one of a mirror, lens, and fiber optic waveguide.

6. The target vapor emission system of claim 1, wherein said wave guide includes at least one of a mirror, lens, and fiber optic waveguide.

7. The target vapor emission system of claim 6, wherein said wave guide is adjustable to increase the area illuminated.

8. The target vapor emission system of claim 1, wherein said source of photon emission is made to be substantially in a limited band of wavelengths between infrared to ultraviolet using at least one of a filter, coating, and covering.

9. The target vapor emission system of claim 1, wherein said source of photon emission has enhanced emission substantially in the infrared by means of conversion of shorter wavelength photons to infrared photons.

10. The target vapor emission system of claim 1, wherein said source of photon emission is separated from said target surface by at least one of a window, semi-transparent window, coated window, and grid.

11. The target vapor emission system of claim 1, wherein the vapor detection instrument comprises at least one taken from the list consisting of a gas chromatograph, an ion mobility spectrometer, a mass spectrometer, a mass-sensitive microsensor, an electron capture detector, a sensor employing optical stimulation, and a semiconductor-based microsensor.

12. A method of inducing emission of target vapor for a vapor detection instrument, comprising:
    generating a pulsed photon emission having multiple wavelengths contained substantially within the infrared to ultraviolet;
    concentrating said pulsed photon emission into a beam; and
    directing said beam towards a target surface to heat the target surface with the pulsed photon emission having multiple wavelengths to increase vapor emissions from the target surface.

13. The method of claim 12, wherein generating a pulsed photon emission includes generating a pulse less than 100 milliseconds in duration.

14. The method of claim 12, wherein directing said photon emission includes modifying the area illuminated.

15. The method of claim 12, further comprising limiting the band of wavelengths of said photon emission.

16. The method of claim 12, further comprising converting shorter wavelength photons in the photon emission to infrared photons.

* * * * *

UNITED STATES PATENT AND TRADEMARK OFFICE
CERTIFICATE OF CORRECTION

PATENT NO. : 7,098,672 B2
APPLICATION NO. : 10/890820
DATED : August 29, 2006
INVENTOR(S) : Belyakov et al.

Page 1 of 1

It is certified that error appears in the above-identified patent and that said Letters Patent is hereby corrected as shown below:

Col. 1, line 21
The following section heading and statement should be inserted:

--STATEMENT OF GOVERNMENT SUPPORT
This invention was made with Government support under contract W909MY-04-C-0002 awarded by the U.S. Department of the Army. The Government has certain rights in the invention.--

Signed and Sealed this

Twenty-ninth Day of December, 2009

David J. Kappos
*Director of the United States Patent and Trademark Office*